US005519118A

United States Patent [19]
Vogelstein et al.

[11] Patent Number: 5,519,118
[45] Date of Patent: May 21, 1996

[54] HUMAN MDM2 PROTEIN INVOLVED IN HUMAN TUMORS

[75] Inventors: Bert Vogelstein; Kenneth Kinzler, both of Baltimore, Md.

[73] Assignee: The Johns Hopkins University, Baltimore, Md.

[21] Appl. No.: 283,911

[22] Filed: Aug. 4, 1994

Related U.S. Application Data

[60] Division of Ser. No. 903,103, Jun. 23, 1992, Pat. No. 5,411,860, which is a continuation-in-part of Ser. No. 867,840, Apr. 7, 1992, abandoned.

[51] Int. Cl.$^6$ ................................................. C07K 14/47
[52] U.S. Cl. ............................... 530/350; 530/388.6
[58] Field of Search ............................... 530/350, 388.6

[56] References Cited

PUBLICATIONS

Farharzadeh et al., "Tumorigenic Potential Associated with Enhanced Expression of a Gene That is Amplified in a Mouse Tumor Cell Line", *The EMBO Journal* 10(6):1565–1569 (1991).

Hinds et al., "Mutant p. 53 DNA Clones From Human Colon Carcinomas Cooperate With Ras in Transforming Primary Rat Cells: A Comparison of the 'Hot Spot' Mutant Phenotypes", *Cell Growth & Differentiation*, 1:561–580 (1990).

Romkes et al., "Cloning and Expression of Complementary DNAs for Multiple Members of the Human Cytochrome P450IIC Subfamily", *Biochemistry* 30:3247–3255 (1991).

Oliner et al., "Amplification of a Gene Encoding a p. 53—Associated Protein in Human Sarcomas", *Nature* 358:80–83 (1992).

Oliner et al., "Oncoprotein MDM2 Conceals the Activation Domain of Tumor Suppressor p. 53", *Nature* 362(6423):857–860 (1993) Abstract.

Leach et al., "p. 53 Mutation and MDM2 Amplification in Human Soft Tissue Sarcomas", *Cancer Research* 53:2231–2234 (1993).

Momand et al., "The mdm–2 Oncogene Product Forms a Complex With the p. 53 Protein and Inhibits p. 53—Mediated Transactivation", *Cell* 89:1237–1245 (1992).

Bueso–Ramo et al., "The Human MDM2 Oncogene is Overexpressed in Leukemias", *Blood*, 2(9):2017–2023 (1993).

*Primary Examiner*—Mindy Fleisher
*Assistant Examiner*—Terry A. McKelvey
*Attorney, Agent, or Firm*—Banner & Allegretti, Ltd.

[57] ABSTRACT

A human gene has been discovered which is genetically altered in human tumor cells. The genetic alteration is gene amplification and leads to a corresponding increase in gene products. Detecting that the gene, designated hMDM2, has become amplified or detecting increased expression of gene products is diagnostic of tumorigenesis. Human MDM2 protein binds to human p53 and appears to allow the cell to escape from p53-regulated growth.

8 Claims, 12 Drawing Sheets

FIG. 1A(1)

```
  1   GCACCGCGCGAGCTTGGCTGCTTCTGGGGC

* AG
 84   GGCCGCGACCCCTCTGACCGAGATCCTGCTG

CGT  GC  GG CTCCGCGCTCCCCG GAAG
168   GTGCCTGGCCCGGAGAGTGGAATGATCCCC

ACC GACACCCCTGGGGGACC    TCG AT
252   GGAGTCTTGAGGGACCCCGACTCCAAGCGC
  1

T    C  G        C  G
336   CCTACTGATGGTGCTGTAACCACCTCACAGA
  9    P  T  D  G  A  V  T  T  S  Q
       S     E        A     S

G       C    A  G       C
420   TTATTAAAGTCTGTTGGTGCACAAAAAGACA
 37    L  L  K  S  V  G  A  Q  K  D
                                  N

A G       C        G G  C
504   CGATTATATGATGAGAAGCAACAACATATTG
 65    R  L  Y  D  E  K  Q  Q  H  I

G                G A
588   GTGAAAGAGCACAGGAAAATATATACCATGA
 93    V  K  E  H  R  K  I  Y  T  M
                                  A

GC        G   AC    G C
672   TCTGTGAGTGAGAACAGGTGTCACCTTGAAG
121    S  V  S  E  N  R  C  H  L  E
       L        S     R  Q  P
```

FIG. 1A(2)

```
CTGTGTGGCCCTGTGTGTCGGAAAGATGGAGCAAGA

AGCCGC GC TTCTC TCG TCGAGCT TG ACGAC
CTTTCGCAGCCAGGAGCACCGTCCCTCCCCGGATTA

GTCGGAA ATGCGC G AAGTAG      CC     T CT
GAGGCCCAGGGCGTCGTGCTTCCGCAGTAGTCAGTC

ACCGCG TTCTCCT C GCCTC       C
GAAAACCCCGGATGGTGAGGAGCAGGCAAATGTGCA
                                M  C

T
TTCCAGCTTCGGAACAAGAGACCCTGGTTAGACCAA
 I  P  A  S  E  Q  E  T  L  V  R  P

C              A  A  A        A
CTTATACTATGAAAGAGGTTCTTTTTTATCTTGGCC
 T  Y  T  M  K  E  V  L  F  Y  L  G
                      I  I        I

G                      C           G
TATATTGTTCAAATGATCTTCTAGGAGATTTGTTTG
 V  Y  C  S  N  D  L  L  G  D  L  F
                                     V

A  T  A  G CT A G      A----
TCTACAGGAACTTGGTAGTAGTCAATCAGCAGGAAT
 I  Y  R  N  L  V  V  V  N  Q  Q  E
                      A     S        -

TG      T C T G    C  CA
GTGGGAGTGATCAAAAGGACCTTGTACAAGAGCTTC
 G  G  S  D  Q  K  D  L  V  Q  E  L
    L           P     L     A  P
```

FIG. 1A(3)

```
                     AGCCGAGCCCGAGGGGC          83    Human  nt

CATG   CGCTCA  G   C                             Mouse  nt
     GTGCGTACGAGCGCCCA                       167    Human  nt GGGCGAGC  GAGACC                                Mouse  nt
     CCCGTGAAGGAAACTGG                       251    Human  nt G                   Mouse  nt
     ATACCAACATGTCTGTA                       335    Human  nt
       N     T    N    M    S    V             8    Human  a.a.
                                                      Mouse  a.a.

A                                             Mouse  nt
     AGCCATTGCTTTTGAAG                        419    Human  nt
       K     P    L    L    L    K            36    Human  a.a.
                                                      Mouse  a.a.

G                   Mouse  nt
     AGTATATTATGACTAAA                        503    Human  nt
       Q     Y    I    M    T    K            64    Human  a.a.
                                                      Mouse  a.a.

A    C    G    T                             Mouse  nt
     GCGTGCCAAGCTTCTCT                        587    Human  nt
       G     V    P    S    F    S            92    Human  a.a.
                                                      Mouse  a.a.

-----       T    C                               Mouse  nt
     CATCGGACTCAGGTACA                        671    Human  nt
       S     S    D    S    G    T           120    Human  a.a.
       -     -                                        Mouse  a.a.

CA                                               Mouse  nt
     AGGAAGAGAAACCTTCA                        755    Human  nt
       Q     E    E    K    P    S           148    Human  a.a.
       P                                              Mouse  a.a.
```

FIG. 1B(1)

```
              TG       AA              TG
756    TCTTCACATTTGGTTTCTAGACCATCT
149      S  S  H  L  V  S  R  P  S
                  D     I     L

G    G  G   CC  G  G      G  GG
840    GGTGAACGACAAAGAAAACGCCACAAA
177      G  E  R  Q  R  K  R  H  K
               H                 R  R

G  CAGCGGCGGCACGAGCA CAGT
924    ATATGT---------------TGTGAA
205      I  C  -  -  -  -  -  C  E
         M     S  G  G  T  S  S  S

G     T        CC
993    GTAAGTGAACATTCAGGTGATTGGTTG
228      V  S  E  H  S  G  D  W  L
                              C

G        C     G     C
1077   TCAGAAGATTATAGCCTTAGTGAAGAA
256      S  E  D  Y  S  L  S  E  E
                                 D

A  A   C         C  T
1161   GGGGAGAGTGATACAGATTCATTTGAA
284      G  E  S  D  T  D  S  F  E

T              C   A
1245   AATCCCCCCCTTCCATCACATTGCAAC
312      N  P  P  L  P  S  H  C  N
                                    K

A
1329   GAAATCTCTGAGAAAGCCAAACTGGAA
340      E  I  S  E  K  A  K  L  E
```

FIG. 1B(2)

```
                T C                                    G
ACCTCATCTAGAAGGAGAGCAATTAGTGAGACAGAAGAA
  T  S  S  R  R  R  A  I  S  E  T  E  E
              S

------------         G         CCG         G
TCTGATAGTATTTCCCTTTCCTTTGATGAAAGCCTGGCT
  S  D  S  I  S  L  S  F  D  E  S  L  A
  -  -  -  -              P           G

C     C        C G C   A        C     C
AGAAGCAGTAGCAGTGAATCTACAGGGACGCCATCGAAT
  R  S  S  S  S  E  S  T  G  T  P  S  N
  S                          E           H

T                    C G
GATCAGGATTCAGTTTCAGATCAGTTTAGTGTAGAATTT
  D  Q  D  S  V  S  D  Q  F  S  V  E  F

G C G           G           C     GG
GGACAAGAACTCTCAGATGAAGATGATGAGGTATATCAA
  G  Q  E  L  S  D  E  D  D  E  V  Y  Q
     H                                R

G              G                       G  T
GAAGATCCTGAAATTTCCTTAGCTGACTATTGGAAATGC
  E  D  P  E  I  S  L  A  D  Y  W  K  C
  G

C  A              C        A  C
AGATGTTGGGCCCTTCGTGAGAATTGGCTTCCTGAAGAT
  R  C  W  A  L  R  E  N  W  L  P  E  D
        T                             D

G T  G  A        A        G     G
AACTCAACACAAGCTGAAGAGGGCTTTGATGTTCCTGAT
  N  S  T  Q  A  E  E  G  F  D  V  P  D
        A                 L
```

FIG. 1B(3)

```
         CA          GC     C             Mouse nt
    AATTCAGATGAATTATCT              839   Human nt
      N  S  D  E  L  S              176   Human a.a.
         T        P                       Mouse a.a.

AGC  G                        Mouse nt
    CTGTGTGTAATAAGGGAG              923   Human nt
      L  C  V  I  R  E              204   Human a.a.
            E  L                          Mouse a.a.

A         C  A     C                Mouse nt
    CCGGATCTTGATGCTGGT              992   Human nt
      P  D  L  D  A  G              227   Human a.a.
      Q           D                       Mouse a.a.

G        G                    Mouse nt
    GAAGTTGAATCTCTCGAC             1076   Human nt
      E  V  E  S  L  D              255   Human a.a.
                                          Mouse a.a.

C  A  C        A                    Mouse nt
    GTTACTGTGTATCAGGCA             1160   Human nt
      V  T  V  Y  Q  A              283   Human a.a.
                     T                    Mouse a.a.

C                                   Mouse nt
    ACTTCATGCAATGAAATG             1244   Human nt
      T  S  C  N  E  M              311   Human a.a.
                                          Mouse a.a.

G              T                 Mouse nt
    AAAGGGAAAGATAAAGGG             1228   Human nt
      K  G  K  D  K  G              339   Human a.a.
                     V                    Mouse a.a.

G C       GCTG  C    A              Mouse nt
    TGTAAAAAAACTATAGTG             1412   Human nt
      C     K  K  T  I  V           367   Human a.a.
      G           L  T  E                 Mouse a.a.
```

FIG. IC(1)

```
              G T A     C        C         G
1413   AATGATTCCAGAGTCATGTGTTGAGGAA
 368     N D S R E S C V E E
              A K     P        A

C   A     G        C C         G
1494   TCTCAGCCATCAACTTCTAGTAGCATTATT
 395     S Q P S T S S S I I
                                       V

C                       C CT      G
1578   GAAGAGAGTGTGGAATCTAGTTTGCCCCTT
 423     E E S V E S S L P L
         D                     F S

T C     G T      C C   T A
1662   GTCCATGGCAAAACAGGACATCTTATGGCC
 451     V H G K T G H L M A
                                         S

G       C                        G
1746   AGACAACCAATTCAAATGATTGTGCTAACT
 479     R Q P I Q M I V L T
                                           S

1830   TAACCCTAGGAATTTAGACAACCTGAAATT
1914   TTAGTATAATTGACCTACTTTGGTAGTGGA
1998   ACTCCTAATTTTAAATAATTTCTACTCTGT
2082   ATGTAACTTATTATTTTTTTGAGACCGAG
2166   CTCTGCCCTCCCGGGTTCGCACCATTCTC
2250   TAATTTTTTGTACTTTTAGTAGAGACAGGG
2334   CTCGGCCTCCCAAAGTGCTGGGATTACAGG
```

FIG. 1C(2)

```
  G CAGC    G  G  GGCCGA      GA GC C TG   C
AAT---GATGATAAAATTACACAAGCTTCACAATCAC
  N  -  D  D  K  I  T  Q  A  S  Q  S
     D     S  E  E     A  E     T  P  L

AGC                G--- A
TATAGCAGCCAAGAAGATGTGAAAGAGTTTGAAAGGG
  Y  S  S  Q  E  D  V  K  E  F  E  R
              S              L  -  K

C     A           C  C  G  G    G
AATGCCATTGAACCTTGTGTGATTTGTCAAGGTCGAC
  N  A  I  E  P  C  V  I  C  Q  G  R

T  C  G                    A    A  C
TGCTTTACATGTGCAAAGAAGCTAAAGAAAAGGAATA
  C  F  T  C  A  K  K  L  K  K  R  N

C  AA    C           CTCA A  A   T
TATTTCCCCTAGTTGACCTG---TCTATAAGAGAATT
  Y  F  P
        N

TATTCACATATATCAAAGTGAGAAAATGCCTCAATTC
ATAGTGAATACTTACTATAATTTGACTTGAATATGTA
CTTAAATGAGAAGTACTTGGTTTTTTTTTTCTTAAAT
TCTTGCTCTGTTACCCAGGCTGGAGTGCAGTGGGTGA
CTGCCTCAGCCTCCCAATTAGCTTGGCCTACAGTCAT
TTTCACCGTGTTAGCCAGGATGGTCTCGATCTCCTGA
CATGAGCCACCG
```

FIG. 1C(3)

```
    G   G       C                        Mouse nt
AAGAAAGTGAAGACTAT           1493         Human nt
 Q   E   S   E   D   Y       394         Human a.a.
                 D                       Mouse a.a.

G       G GC                         Mouse nt
AAGAAACCCAAGACAAA           1577         Human nt
 E   E   T   Q   D   K       422         Human a.a.
                 H                       Mouse a.a.

C                               Mouse nt
CTAAAAATGGTTGCATT           1661         Human nt
 P   K   N   G   C   I       450         Human a.a.
                                         Mouse a.a.

G    C                     Mouse nt
AGCCCTGCCCAGTATGT           1745         Human nt
 K   P   C   P   V   C       478         Human a.a.
                                         Mouse a.a.

T                  *                    Mouse nt
ATATATTTCTAACTATA           1829         Human nt
                             491         Human a.a.
                                         Mouse a.a.

ACATAGATTTCTTCTCT           1913         Human nt
GCTCATCCTTTACACCA           1997         Human nt
ATGTATATGACATTTAA           2081         Human nt
TCTTGGCTCACTGCAAG           2165         Human nt
CTGCCACCACACCTGGC           2249         Human nt
CCTCGTGATCCGCCCAC           2333         Human nt
                             2372        Human nt
```

HUMAN MDM2 PROTEIN INVOLVED IN HUMAN TUMORS

This application is a division of application Ser. No. 07/903,103, filed Jun. 23, 1992, which issued as U.S. Pat. No. 5,411,860 on May 2, 1995, which is a continuation-in-part of application Ser. No. 07/867,840 filed Apr. 7, 1992 (now abandoned).

FIELD OF THE INVENTION

The invention relates to the area of cancer diagnostics and therapeutics. More particularly, the invention relates to the detection of a gene which is amplified in certain human tumors.

BACKGROUND OF THE INVENTION

According to the Knudson model for tumorigenesis (Cancer Research, 1985, vol. 45, p. 1482), there are tumor suppressor genes in all normal cells which, when they become non-functional due to mutation, cause neoplastic development. Evidence for this model has been found in cases of retinoblastoma and colorectal tumors. The implicated suppressor genes in these tumors, RB and p53 respectively, were found to be deleted or altered in many of the tumors studied.

The p53 gene product, therefore, appears to be a member of a group of proteins which regulate normal cellular proliferation and suppression of cellular transformation. Mutations in the p53 gene have been linked to tumorigenesis, suggesting that alterations in p53 protein function are involved in cellular transformation. The inactivation of the p53 gene has been implicated in the genesis or progression of a wide variety of carcinomas (Nigro et al., 1989, Nature 342:705–708), including human colorectal carcinoma (Baker et al., 1989, Science 244:217–221), human lung cancer (Takahashi et al., 1989, Science 246:491–494; Iggo et al., 1990, Lancet 335:675–679), chronic myelogenous leukemia (Kelman et al, 1989, Proc. Natl. Acad. Sci. USA 86:6783–6787) and osteogenic sarcomas (Masuda et al., 1987, Proc. Natl. Acad. Sci. USA 84:7716–7719).

While there exists an enormous body of evidence linking p53 gene mutations to human tumorigenesis (Hollstein et al., 1991, Science 253:49–53) little is known about cellular regulators and mediators of p53 function.

Hinds et al. (Cell Growth & Differentiation, 1990, 1:571–580), found that p53 cDNA clones, containing a point mutation at amino acid residue 143, 175, 273 or 281, cooperated with the activated ras oncogene to transform primary rat embryo fibroblasts in culture. These mutant p53 genes are representative of the majority of mutations found in human cancer. Hollstein et al., 1991, Science 253:49–53. The transformed fibroblasts were found to produce elevated levels of human p53 protein having extended half-lives (1.5 to 7 hours) as compared to the normal (wild-type) p53 protein (20 to 30 minutes).

Mutant p53 proteins with mutations at residue 143 or 175 form an oligomeric protein complex with the cellular heat shock protein hsc70. While residue 273 or 281 mutants do not detectably bind hsc70, and are poorer at producing transformed foci than the 175 mutant, complex formation between mutant p53 and hsc70 is not required for p53-mediated transformation. Complex formation does, however, appear to facilitate this function. All cell lines transformed with the mutant p53 genes are tumorigenic in athymic (nude) mice. In contrast, the wild-type human p53 gene does not possess transforming activity in cooperation with ras. Tuck and Crawford, 1989, Oncogene Res. 4:81–96.

Hinds et al. supra also expressed human p53 protein in transformed rat cells. When the expressed human p53 was immunoprecipitated with two p53 specific antibodies directed against distinct epitopes of p53, an unidentified $M_r$ 90,000 protein was coimmunoprecipitated. This suggested that the rat $M_r$ 90,000 protein is in a complex with the human p53 protein in the transformed rat cell line.

As mentioned above, levels of p53 protein are often higher in transformed cells than normal cells. This is due to mutations which increase its metabolic stability (Oven et al., 1981, Mol. Cell. Biol. 1:101–110; Reich et al., (1983), Mol. Cell. Biol. 3:2143–2150). The stabilization of p53 has been associated with complex formation between p53 and viral or cellular proteins. (Linzer and Levine, 1979, Cell 17:43–52; Crawford et al., 1981, Proc. Natl. Acad. Sci. USA 78:41–45; Dippold et al., 1981, Proc. Natl. Acad. Sci. USA 78:1695–1699; Lane and Crawford, 1979, Nature (Lond.) 278:261–263; Hinds et al., 1987, Mol. Cell. Biol. 7:2863–2869; Finlay et al., 1988, Mol. Cell. Biol. 8:531–539; Sarnow et al., 1982, Cell. 28:387–394; Gronostajski et al., 1984, Mol. Cell. Biol. 4:442–448; Pinhasi-Kimhi et al., 1986, Nature (Lond.) 320: 182–185; Ruscetti and Scolnick, 1983, J. Virol. 46: 1022–1026; Pinhasi and Oren, 1984, Mol. Cell. Biol. 4:2180–2186; and Sturzbecher et al., 1987, Oncogene 1:201–211.) For example, p53 protein has been observed to form oligomeric protein complexes with the SV40 large T antigen, the adenovirus type 5 E1B-$M_r$ 55,000 protein, and the human papilloma virus type 16 or 18 E6 product. Linzer and Levine, 1979, Cell 17:43–52; Lane and Crawford, 1979, Nature, 278:261–263; Sarnow et al., 1982, Cell 28:387–394; Werness et al., 1990, Science, 248:76–79. Similarly, complexes have been observed of $p105^{RB}$ (the product of the retinoblastoma susceptibility gene) with T antigen (DeCaprio et al., 1988, Cell 54:275–283), the adenovirus EIA protein (Whyte et al., 1988, Nature 334:124–129) and the E7 protein of human papilloma virus 16 or 18 (Münger et al., 1989, EMBO J. 8:4099–4105). It has been suggested that interactions between these viral proteins and $p105^{RB}$ inactivate a growth-suppressive function of $p105^{RB}$, mimicking deletions and mutations commonly found in the RB gene in tumor cells. In a similar fashion, oligomeric protein complex formation between these viral proteins and p53 may eliminate or alter the function of p53. Finlay et at., 1989, Cell 57: 1083–1093.

Fakharzadeh et at. (EMBO J. 1991, 10:1565–1569) analyzed amplified DNA sequences present in a tumorigenic mouse cell line (i.e., 3T3DM, a spontaneously transformed derivative of mouse Balb/c cells). Studies were conducted to determine whether any of the amplified genes induced tumorigenicity following introduction of the amplified genes into a nontransformed recipient cell (e.g., mouse NIH3T3 or Rat2 cells). The resulting cell lines were tested for tumorigenicity in nude mice. A gene, designated MDM2, which is amplified more than 50-fold in 3T3DM cells, induced tumorigenicity when overexpressed in NIH3T3 and Rat 2 cells. From the nucleotide and predicted amino acid sequence of mouse MDM2 (mMDM2), Fakharzadeh speculated that this gene encodes a potential DNA binding protein that functions in the modulation of expression of other genes and, when present in excess, interferes with normal constraints on cell growth.

SUMMARY OF THE INVENTION

It is an object of the invention to provide a method for diagnosing a neoplastic tissue, such as sarcoma, in a human.

It is another object of the invention to provide a cDNA molecule encoding the sequence of human MDM2.

Yet another object of the invention is to provide a preparation of human MDM2 protein which is substantially free of other human cellular proteins.

Still another object of the invention is to provide DNA probes capable of hybridizing with human MDM2 genes or mRNA molecules.

Another object of the invention is to provide antibodies immunoreactive with human MDM2 protein.

Still another object of the invention is to provide kits for detecting amplification or elevated expression of human MDM2.

Yet another object of the invention is to provide methods for identifying compounds which interfere with the binding of human MDM2 to human p53.

A further object of the invention is to provide a method of treating a neoplastic human cell.

It has now been discovered that hMDM2, a heretofore unknown human gene, plays a role in human cancer. The hMDM2 gene has been cloned and the recombinant derived hMDM2 protein shown to bind to human p53 in vitro. hMDM2 has been found to be amplified in some neoplastic cells and the expression of hMDM2-encoded products has been found to be correspondingly elevated in tumors with amplification of this gene. The elevated levels of MDM2 appear to sequester p53 and allow the cell to escape from p53-regulated growth.

BRIEF DESCRIPTION OF THE DRAWINGS

FIG. 1A–C shows the cDNA sequence of human MDM2. In this figure, human and mouse nucleotide (SEQ ID NOS: 1 and 3, respectively) and amino acid sequences (SEQ ID NOS: 2 and 4, respectively) are compared, the mouse sequence being shown only where it differs from the corresponding human sequence.

DETAILED DESCRIPTION OF THE INVENTION

Figure 2:
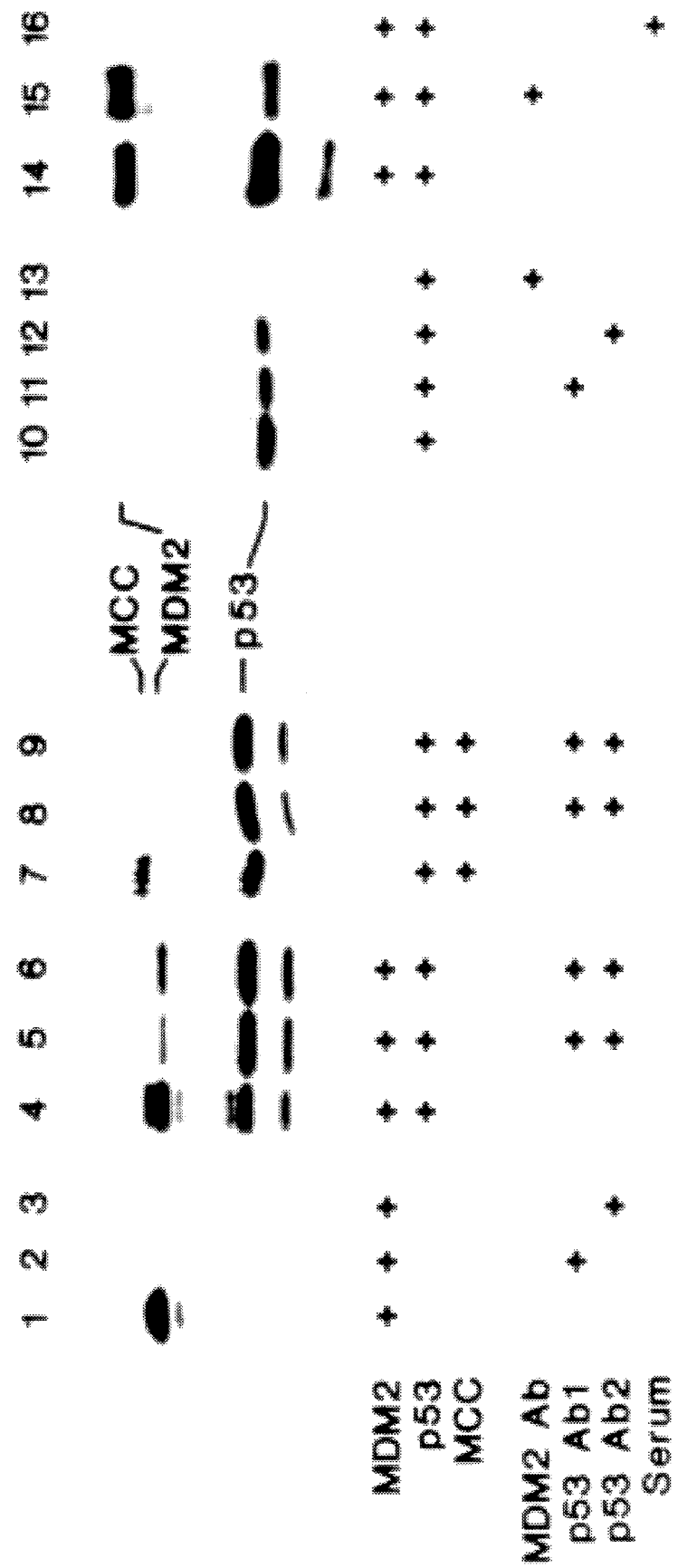
FIG. 2 shows that hMDM2 binds to p53.

It is a discovery of the present invention that a gene exists which is amplified in some human tumors. The amplification of this gene, designated MDM2, is diagnostic of neoplasia or the potential therefor. Detecting the elevated expression of human MDM2-encoded products is also diagnostic of neoplasia or the potential for neoplastic transformation. Over a third of the sarcomas surveyed, including the most common bone and soft tissue forms, were found to have amplified hMDM2 sequences. Expression of hMDM2 was found to be correspondingly elevated in tumors with the gene amplification.

Other genetic alterations leading to elevated hMDM2 expression may be involved in tumorigenesis also, such as mutations in regulatory regions of the gene. Elevated expression of hMDM2 may also be involved in tumors other than sarcomas including but not limited to those in which p53 inactivation has been implicated. These include colorectal carcinoma, lung cancer and chronic myelogenous leukemia.

According to one embodiment of the invention, a method of diagnosing a neoplastic tissue in a human is provided. Tissue or body fluid is isolated from a human, and the copy number of human MDM2 genes is determined. Alternatively, expression levels of human MDM2 gene products can be determined. These include protein and mRNA.

Body fluids which may be tested include urine, serum, blood, feces, saliva, and the like. Tissues suspected of being neoplastic are desirably separated from normal appearing tissue for analysis. This can be done by paraffin or cryostat sectioning or flow cytometry, as is known in the art. Failure to separate neoplastic from non-neoplastic cells can confound the analysis. Adjacent non-neoplastic tissue or any normal tissue can be used to determine a base-line level of expression or copy number, against which the amount of hMDM2 gene or gene products can be compared.

The human MDM2 gene is considered to be amplified if the cell contains more than the normal copy number (2) of this gene per genome. The various techniques for detecting gene amplification are well known in the art. Gene amplification can be determined, for example, by Southern blot analysis, as described in Example 4, wherein cellular DNA from a human tissue is digested, separated, and transferred to a filter where it is hybridized with a probe containing complementary nucleic acids. Alternatively, quantitative polymerase chain reaction (PCR) employing primers can be used to determine gene amplification. Appropriate primers will bind to sequences that bracket human MDM2 coding sequences. Other techniques for determining gene copy number as are known in the art can be used without limitation.

The gene product which is measured may be either mRNA or protein. The term elevated expression means an increase in mRNA production or protein production over that which is normally produced by non-cancerous cells. Although amplification has been observed in human sarcomas, other genetic alterations leading to elevated expression of MDM2 may be present in these or other tumors. Other tumors include those of lung, breast, brain, colorectal, bladder, prostate, liver, skin, and stomach. These, too, are contemplated by the present invention. Non-cancerous cells for use in determining base-line expression levels can be obtained from cells surrounding a tumor, from other humans or from human cell lines. Any increase can have diagnostic value, but generally the mRNA or protein expression will be elevated at least about 3-fold, 5-fold, and in some cases up to about 100-fold over that found in non-cancerous cells. The particular technique employed for detecting mRNA or protein is not critical to the practice of the invention. Increased production of mRNA or protein may be detected, for example, using the techniques of Northern blot analysis or Western blot analysis, respectively, as described in Example 4 or other known techniques such as ELISA, immunoprecipitation, RIA and the like. These techniques are also well known to the skilled artisan.

According to another embodiment of the invention, nucleic acid probes or primers for the determining of human MDM2 gene amplification or elevated expression of mRNA are provided. The probe may comprise ribo- or deoxyfibonucleic acids and may contain the entire human MDM2 coding sequence, a sequence complementary thereto, or fragments thereof. A probe may contain, for example, nucleotides 1–949, or 1–2372 as shown in FIG. 1 (SEQ ID NOS:1). Generally, probes or primers will contain at least about 14 contiguous nucleotides of the human sequence but may desirably contain about 40, 50 or 100 nucleotides. Probes are typically labelled with a fluorescent tag, a radioisotope, or the like to render them easily detectable. Preferably the probes will hybridize under stringent hybridization conditions. Under such conditions they will not hybridize to mouse MDM2. The probes of the invention are complementary to the human MDM2 gene. This means that they share 100% identity with the human sequence.

hMDM2 protein can be produced, according to the invention, substantially free of other human proteins. Provided with the DNA sequence (SEQ ID NO: 1), those of skill in the art can express the cDNA in a non-human cell. Lysates of such cells provide proteins substantially free of other human proteins. The lysates can be further purified, for example, by immunoprecipitation, coprecipitation with p53, or by affinity chromatography.

The antibodies of the invention are specifically reactive with hMDM2 protein. Preferably, they do not cross-react with MDM2 from other species. They can be polyclonal or monoclonal, and can be raised against native hMDM2 or a hMDM2 fusion protein or synthetic peptide. The antibodies are specifically immunoreactive with hMDM2 epitopes which are not present on other human proteins. Some antibodies are reactive with epitopes unique to human MDM2 and not present on the mouse homolog. The antibodies are useful in conventional analyses, such as Western blot analysis, ELISA and other immunological assays for the detection of proteins. Techniques for raising and purifying polyclonal antibodies are well known in the art, as are techniques for preparing monoclonal antibodies. Antibody binding can be determined by methods known in the art, such as use of an enzyme-labelled secondary antibody, staphylococcal protein A, and the like.

According to another embodiment of the invention, interference with the expression of MDM2 provides a therapeutic modality. The method can be applied in vivo, in vitro, or ex vivo. For example, expression may be down-regulated by administering triple-strand forming or antisense oligonucleotides which bind to the hMDM2 gene or mRNA, respectively, and prevent transcription or translation. The oligonucleotides may interact with unprocessed pre-mRNA or processed mRNA. Small molecules and peptides which specifically inhibit MDM2 expression can also be used. Similarly, such molecules which inhibit the binding of MDM2 to p53 would be therapeutic by alleviating the sequestration of p53.

Such inhibitory molecules can be identified by screening for interference of the hMDM2/p53 interaction where one of the binding partners is bound to a solid support and the other partner is labeled. Antibodies specific for epitopes on hMDM2 or p53 which are involved in the binding interaction will interfere with such binding. Solid supports which may be used include any polymers which are known to bind proteins. The support may be in the form of a filter, column packing matrix, beads, and the like. Labeling of proteins can be accomplished according to any technique known in the art. Radiolabels, enzymatic labels, and fluorescent labels can be used advantageously. Alternatively, both hMDM2 and p53 may be in solution and bound molecules separated from unbound subsequently. Any separation technique known in the art may be employed, including immunoprecipitation or immunoaffinity separation with an antibody specific for the unlabeled binding partner.

A cDNA molecule containing the coding sequence of hMDM2 can be used to produce probes and primers. In addition, it can be expressed in cultured cells, such as E. coli, to yield preparations of hMDM2 protein substantially free of other human proteins. The proteins produced can be purified, for example, with immunoaffinity techniques using the antibodies described above.

Kits are provided which contain the necessary reagents for determining gene copy number, such as probes or primers specific for the hMDM2 gene, as well as written instructions. The instructions can provide calibration curves to compare with the determined values. Kits are also provided to determine elevated expression of mRNA (i.e., containing probes) or hMDM2 protein (i.e., containing antibodies). Instructions will allow the tester to determine whether the expression levels are elevated. Reaction vessels and auxiliary reagents such as chromogens, buffers, enzymes, etc. may also be included in the kits.

The human MDM2 gene has now been identified and cloned. Recombinant derived hMDM2 has been shown to bind to human p53. Moreover, it has been found that hMDM2 is amplified in some sarcomas. The amplification leads to a corresponding increase in MDM2 gene products. Such amplification is associated with the process of tumorigenesis. This discovery allows specific assays to be performed to assess the neoplastic or potential neoplastic status of a particular tissue.

The following examples are provided to exemplify various aspects of the invention and are not intended to limit the scope of the invention.

EXAMPLE 1

To obtain human cDNA clones, a cDNA library was screened with a murine MDM2 (mMDM2) cDNA probe. A cDNA library was prepared by using polyadenylated RNA isolated from the human colonic carcinoma cell line CaCo-2 as a template for the production of random hexamer primed double stranded cDNA. Gubler and Hoffmann, 1983, Gene 25:263–268. The cDNA was ligated to adaptors and then to the lambda YES phage vector, packaged, and plated as described by Elledge et al. (Proc. Natl. Acad. Sci. USA, 1991, 88:1731–1735). The library was screened initially with a $^{32}$P-labelled (Feinberg and Vogelstein, 1983, Anal. Biochem. 132:6–13) mMDM2 cDNA probe (nucleotides 259 to 1508 (SEQ ID NO: 3) (Fakharzadeh et al., 1991, EMBO J. 10:1565–1569)) and then rescreened with an hMDM2 cDNA clone containing nucleotides 40 to 702 (SEQ ID NO: 1).

Twelve clones were obtained, and one of the clones was used to obtain thirteen additional clones by re-screening the same library. In total, twenty-five clones were obtained, partially or totally sequenced, and mapped. Sequence analysis of the twenty-five clones revealed several cDNA forms indicative of alternative splicing. The sequence shown in FIG. 1 (SEQ ID NO: 1) is representative of the most abundant class and was assembled from three clones: c14-2 (nucleotides 1-949), c89 (nucleotides 467-1737), and c33 (nucleotides 390-2372). The 3' end of the untranslated region has not yet been cloned in mouse or human. The 5' end is likely to be at or near nucleotide 1. There was an open reading frame extending from the 5' end of the human cDNA sequence to nucleotide 1784. Although the signal for translation initiation could not be unambiguously defined, the ATG at nucleotide 312 was considered the most likely position for several reasons. First, the sequence similarity between hMDM2 and mMDM2 fell off dramatically upstream of nucleotide 312. This lack of conservation in an otherwise highly conserved protein suggested that the sequences upstream of the divergence may not code for protein. Second, an anchored polymerase chain reaction (PCR) approach was employed in an effort to acquire additional upstream cDNA sequence. Ochman et al., 1985, In: PCR *Technology: Principles and Applications for DNA Amplification* (Erlich, ed.) pp. 105–111 (Stockton, N.Y.). The 5' ends of the PCR derived clones were very similar (within 3 bp) to the 5' ends of clones obtained from the cDNA library, suggesting that the 5' end of the hMDM2 sequence shown in FIG. 1 (SEQ ID NO: 1) may represent the 5' end of the transcript. Third, in vitro translation of the sequence shown in FIG. 1, beginning with the methionine encoded by the nucleotide 312 ATG, generated a protein similar in size to that observed in human cells.

In FIG. 1, hMDM2 and mMDM2 nucleotide (SEQ ID NOS: 1 and 3 respectively) and amino acid (SEQ ID NOS: 2 and 4, respectively) sequences are compared. The mouse sequence is only shown where it differs from the corresponding human sequence. Asterisks mark the 5' and 3' boundaries of the previously published mMDM2 cDNA. Fakharzadeh et al., 1991, EMBO J. 10:1565–1569. Dashes indicate insertions. The mouse and human amino acid sequences are compared from the putative translation start site at nucleotide 3 12 through the conserved stop codon at nucleotide 1784.

Comparison of the human and mouse MDM2 coding regions revealed significant conservation at the nucleotide (80.3%) and amino acid (80.4%) levels. Although hMDM2 and mMDM2 bore little similarity to other genes recorded in current databases, the two proteins shared several motifs. These included a basic nuclear localization signal (Tanaka, 1990, FEBS Letters 271:41–46) at codons 181 to 185, several casein kinase II serine phosphorylation sites (Pinna, 1990, Biochem. et. Biophys. Acta. 1054:267–284) at codons 166 to 169, 192 to 195, 269 to 272, and 290 to 293, an acidic activation domain (Ptashne, 1988, Nature 355:683–689) at codons 223 to 274, and two metal binding sites (Harrison, 1991, Nature 353:715) at codons 305 to 322 and 461 to 478, neither of which is highly related to known DNA binding domains. The protein kinase A domain noted in mMDM2 (Fakharzadeh et al., 1991, EMBO J. 10:1565–1569) was not conserved in hMDM2.

EXAMPLE 2

To determine whether the hMDM2 protein could bind to human p53 protein in vitro, an hMDM2 expression vector was constructed from the cDNA clones. The hMDM2 expression vector was constructed in pBluescript SK+(Stratagene) from overlapping cDNA clones. The construct contained the sequence shown in FIG. 1 (SEQ ID NO: 1) from nucleotide 312 to 2176. A 42 bp black beetle virus ribosome entry sequence (Dasmahapatra et at., 1987, Nucleic Acid Research 15:3933) was placed immediately upstream of this hMDM2 sequence in order to obtain a high level of expression. This construct, as well as p53 (El-Deriy et al., 1992, Nature Genetics, in press) and MCC (Kinzler et al., 1991, Science 251:1366–1370)constructs in pBluescript SK+, were transcribed with T7 RNA polymerase and translated in a rabbit reticulocyte lysate (Promega) according to the manufacturer's instructions.

Although the predicted size of the protein generated from the construct was only 55.2 kd (extending from the methionine at nucleotide 312 to nucleotide 1784 (SEQ ID NO:1)), in vitro translated protein migrated at approximately 95 kilodaltons.

Ten µl of lysate containing the three proteins (hMDM2, p53 and MCC), alone or mixed in pairs, were incubated at 37° C. for 15 minutes. One microgram (10 µl) of p53 Ab 1 (monoclonal antibody specific for the C-terminus of p53) or Ab2 (monoclonal antibody specific for the N-terminus of p53) (Oncogene Science), or 5 µl of rabbit serum containing MDM2 Ab (polyclonal rabbit anti-hMDM2 antibodies) or preimmune rabbit serum (obtained from the rabbit which produced the hMDM2 Ab), were added as indicated. The polyclonal rabbit antibodies were raised against an *E. coli*-produced hMDM2-glutathione S-transferase fusion protein containing nucleotides 390 to 816 of the hMDM2 cDNA. Ninety µl of RIPA buffer (10 mM tris [pH 7.5], 1% sodium deoxycholate, 1% NP40, 150 mM NaCl, 0.1% SDS), SNNTE buffer (Levin and George, 1992, submitted for publication), or Binding Buffer (El-Deriy et al., 1992, Nature Genetics, in press) were then added and the mixtures allowed to incubate at 4° C. for 2 hours.

Two milligrams of protein A sepharose were added to each tube, and the tubes were rotated end-over-end at 4° C. for 1 hour. After pelleting and washing, the immunoprecipitates were subjected to SDS-polyacrylamide gel electrophoresis and the dried gels autoradiographed for 10 to 60 minutes in the presence of Enhance (New England Nuclear).

FIG. 2 shows the co-precipitation of hMDM2 and p53. The three buffers produced similar results, although the co-precipitation was less efficient in SNNTE buffer containing 0.5M NaCl (FIG. 2, lanes 5 and 8) than in Binding Buffer containing 0.1M NaCl (FIG. 2 lanes 6 and 9).

In vitro translated hMDM2, p53 and MCC proteins were mixed as indicated above and incubated with p53 Abl, p53 Ab2, hMDM2 Ab, or preimmune serum. Lanes 1, 4, 7, 10 and 14 contain aliquots of the protein mixtures used for immunoprecipitation. The bands running slightly faster than p53 are polypeptides produced from internal translation initiation sites.

The hMDM2 protein was not immunoprecipitated with monoclonal antibodies to either the C-terminal or N-terminal regions of p53 (FIG. 2, lanes 2 and 3). However, when in vitro translated human p53 was mixed with the hMDM2 translation product, the anti-p53 antibodies precipitated hMDM2 protein along with p53, demonstrating an association in vitro (FIG. 2, lanes 5 and 6). As a control, a protein of similar electrophoretic mobility from another gene (MCC (Kinzler et al., 1991, Science 251: 1366–1370) ) was mixed with p53. No co-precipitation of the MCC protein was observed (FIG. 2, lanes 8 and 9). When an in vitro translated mutant form of p53 ($175^{his}$) was mixed with hMDM2 protein, a similar co-precipitation of hMDM2 and p53 proteins was also observed.

In the converse of the experiments described above, the anti-hMDM2 antibodies immunoprecipitated p53 when mixed with hMDM2 protein (FIG. 2, lane 15) but failed to precipitate p53 alone (FIG. 5, lane 13). Preimmune rabbit serum failed to precipitate either hMDM2 or p53 (FIG. 2, lane 16).

EXAMPLE 3

In order to ascertain the chromosomal localization of hMDM2, somatic cell hybrids were screened with an hMDM2 cDNA probe. A human-hamster hybrid containing only human chromosome 12 was found to hybridize to the probe. Screening of hybrids containing portions of chromosome 12 (Turc-Carel et al., 1986, Cancer Genet. Cytogenet. 23:291–299) with the same probe narrowed the localization to chromosome 12q12–14.

EXAMPLE 4

Previous studies have shown that this region of chromosome 12 is often aberrant in human sarcomas. Mandahl et al., 1987, Genes Chromosomes & Cancer 1:9–14; Turc-Carel et al., 1986, Cancer Genet. Cytogenet. 23:291–299; Meltzer et al., 1991, Cell Growth & Differentiation 2:495–501. To evaluate the possibility that hMDM2 was genetically altered in such cancers, Southern blot analysis was performed.

Figure 3:
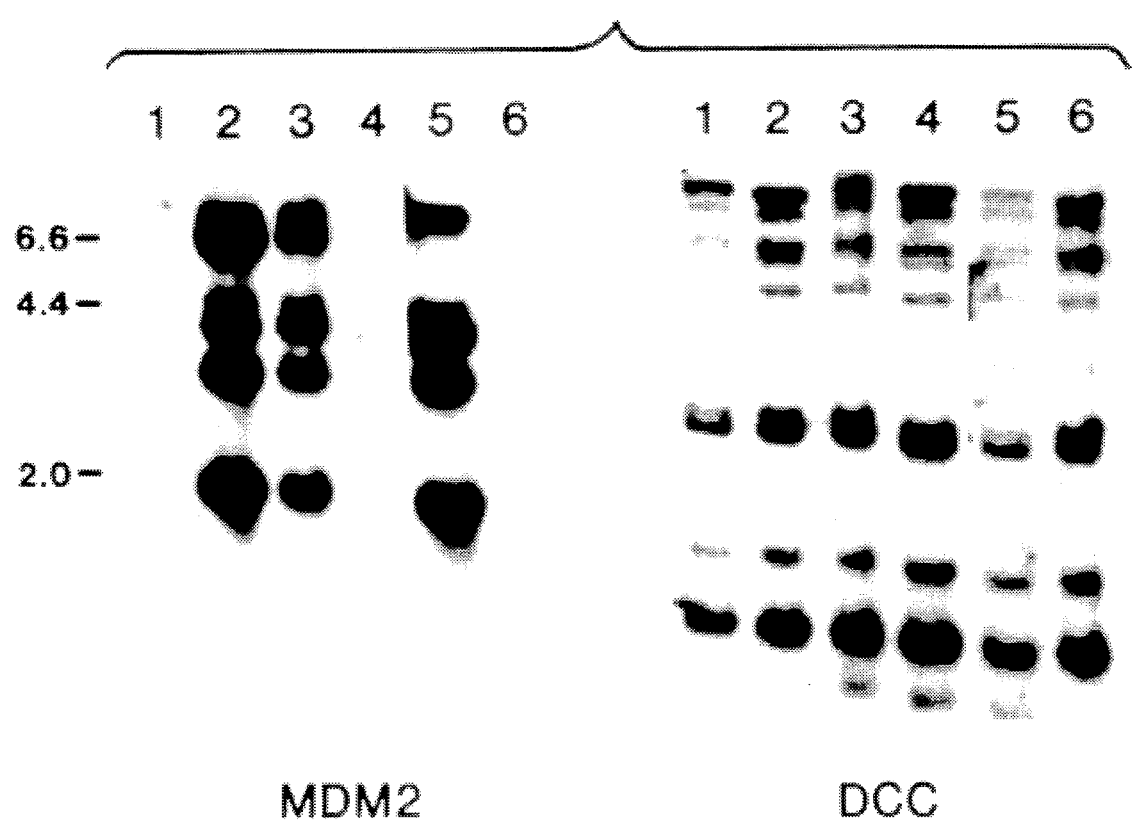
FIG. 3 illustrates the amplification of the hMDM2 gene in sarcomas.

FIG. 3 shows examples of the amplification of the hMDM2 gene in sarcomas. Cellular DNA (5 µg) was digested with EcoRI, separated by agarose gel electrophoresis, and transferred to nylon as described by Reed and Mann (Nucl. Acids Res., 1985, 13:7207–7215). The cellular DNA was derived from five primary sarcomas (lanes 1–4, 6) and one sarcoma cell line (OsA-Cl, lane 5). The filters were then hybridized with an hMDM2 cDNA fragment probe nucleotide 1-949 (see FIG. 1 or SEQ ID NO: 1), or to a control probe which identifies fragments of similar size (DCC gene, 1.65 cDNA fragment). Fearon, 1989, Science 247:49–56. Hybridization was performed as described by Vogelstein et al. (Cancer Research, 1987, 47:4806–4813). A striking amplification of hMDM2 sequences was observed in several of these tumors. (See FIG. 3, lanes 2, 3 and 5). Of 47 sarcomas analyzed, 17 exhibited hMDM2 amplification ranging from 5 to 50 fold. These tumors included 7 to 13 liposarcomas, 7 of 22 malignant fibrous histiocytomas (MFH), 3 of 11 osteosarcomas, and 0 and 1 rhabdomyosarcomas. Five benign soft tissue tumors (lipomas) and twenty-seven carcinomas (colorectal or gastric) were also tested by Southern blot analysis and no amplification was observed.

EXAMPLE 5

This example illustrates that gene amplification is associated with increased expression.

Figure 4A:
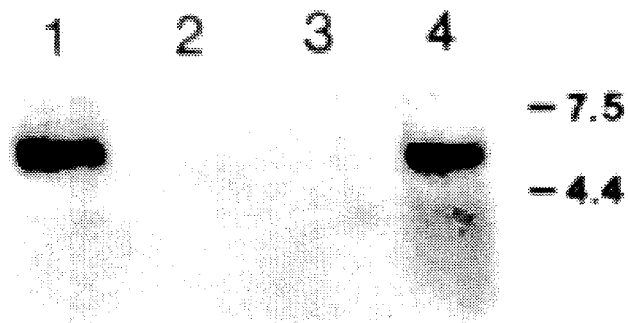
FIG. 4A–C illustrates hMDM2 expression.

FIG. 4A illustrates hMDM2 expression as demonstrated by Northern blot analysis. Because of RNA degradation in the primary sarcomas, only the cell lines could be productively analyzed by Northern blot. RNA was separated by electrophoresis in a MOPS-formaldehyde gel and electrophoretically transferred to nylon filters. Transfer and hybridization were performed as described by Kinzler et at. (Nature, 1988, 332:371–374). The RNA was hybridized to the hMDM2 fragment described in FIG. 3. Ten µg of total RNA derived, respectively, from two sarcoma cell lines (OsA-CL, lane 1 and RC13, lane 2) and the colorectal cancer cell line (CaCo-2) used to make the cDNA library (lane 3). Lane 4 contains 10 µg of polyadenylated CaCo-2 RNA. RNA sizes are shown in kb. In the one available sarcoma cell line with hMDM2 amplification, a single transcript of approximately 5.5 kb was observed (FIG. 4A, lane 1). The amount of this transcript was much higher than in a sarcoma cell line without amplification (FIG. 4A, lane 2) or in a carcinoma cell line (FIG. 4A, lane 3). When purified mRNA (rather than total RNA) from the carcinoma cell line was used for analysis, an hMDM2 transcript of 5.5 kb could also be observed (FIG. 4A, lane 4).

Figure 4B:
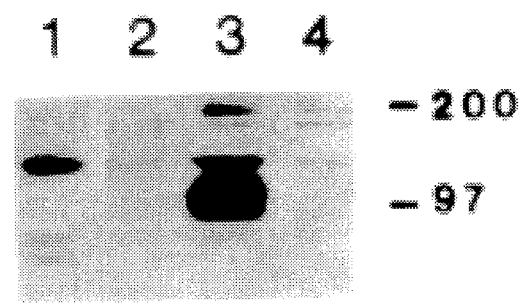

FIG. 4B illustrates hMDM2 expression as demonstrated by Western blot analysis of the sarcoma cell lines RC13 (lane 1), OsA-CL (lane 3), HOS (lane 4), and the carcinoma cell line CaCo-2 (lane 2).

Figure 4C:
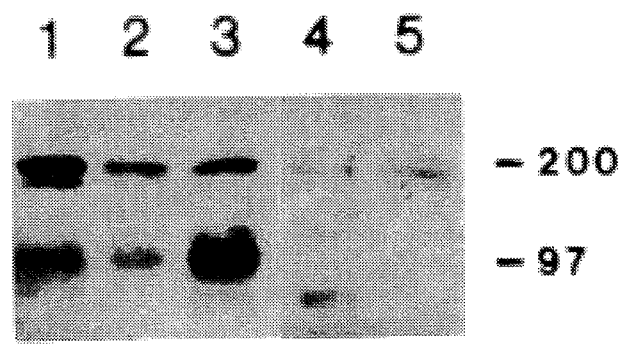

FIG. 4C illustrates hMDM2 expression as demonstrated by Western blot analysis of primary sarcomas. Lanes 1 to 3 contain protein from sarcomas with hMDM2 amplifications, and lanes 4 and 5 contain protein from sarcomas without hMDM2 amplification.

Western blots using affinity purified MDM2 Ab were performed with 50 µg protein per lane as described by Kinzler et al. (Mol. Cell. Biol., 1990, 10:634–642), except that the membranes were blocked in 10% nonfat dried milk and 10% goat serum, and secondary antibodies were coupled to horseradish peroxidase, permitting chemiluminescent detection (Amersham ECL). MDM2 Ab was affinity purified with a pATH-hMDM2 fusion protein using methods described in Kinzler et al. (Mol. Cell. Biol., 1990, 10:634–642). Non-specifically reactive proteins of 85, 120 and 200 kd were observed in all lanes, irrespective of hMDM2 amplification status. hMDM2 proteins, of 97 kd, were observed only in the hMDM2-amplified tumors. Protein marker sizes are shown in kd.

A protein of approximately 97 kilodaltons was expressed at high levels in the sarcoma cell line with hMDM2 amplification (FIG. 4B, lane 3), whereas no expression was evident in two sarcoma cell lines without amplification or in the carcinoma cell line (FIG. 4B, lanes 1, 2 and 4). Five primary sarcomas were also examined by Western blot analysis. Three primary sarcomas with amplification expressed the same size protein as that observed in the sarcoma cell line (FIG. 4C, lanes 1–3), while no protein was observed in the two sarcomas without amplification (FIG. 4C, lanes 4 and 5).

Expression of the hMDM2 RNA in the sarcoma with amplification was estimated to be at least 30 fold higher than that in the other lines examined. This was consistent with the results of Western blot analysis.

The above examples demonstrate that hMDM2 binds to p53 in vitro and is genetically altered (i.e., amplified) in a significant fraction of sarcomas, including MFH, liposarcomas, and osteosarcomas. These are the most common sarcomas of soft tissue and bone. Weiss and Enzinger, 1978, Cancer 41:2250–2266; Malawer et al., 1985, In: *Cancer: Principles and Practice of Oncology*, DeVita et al., Eds., pp. 1293–1342 (Lippincott, Philadelphia).

Human MDM2 amplification is useful for understanding the pathogenesis of these often lethal cancers.

MDM2 may functionally inactivate p53 in ways similar to those employed by virally encoded oncoproteins such as SV40 T-antigen, adenovirus E1B, and HPV E6. Lane and Bechimol, 1990, Genes and Development 4:1–8; Werness et al., 1990, Science 248:76. Consistent with this hypothesis, no sarcomas with hMDM2 amplification had any of the p53 gene mutations that occur commonly in other tumors. hMDM2 amplification provides a parallel between viral carcinogenesis and the naturally occurring genetic alterations underlying sporadic human cancer. The finding that expression of hMDM2 is correspondingly elevated in tumors with amplification of the gene are consistent with the finding that MDM2 binds to p53, and with the hypothesis that overexpression of MDM2 in sarcomas allows escape from p53 regulated growth control. This mechanism of tumorigenesis has striking parallels to that previously observed for virally induced tumors (Lane and Bechimol, 1990, Genes and Development 4:1–8; Werness et al., 1990, Science 248:76), in which vital oncogene products bind to and functionally inactivate p53.

We claim:

1. A composition comprising human MDM2 protein and a buffer, said protein consisting of the sequence of SEQ ID NO:2, wherein said protein is produced in a non-human cell.

2. A composition comprising human MDM2 protein and a buffer, said protein consisting of the sequence of SEQ ID NO:2.

3. A composition comprising human MDM2 protein and a buffer, said protein consisting of the sequence of SEQ ID NO:2, wherein said protein is made in an in vitro transcription and translation system.

4. The composition of claim 2, wherein said human MDM2 protein is purified from other proteins using antibodies specifically immunoreactive with human MDM2 epitopes.

5. An isolated human MDM2 protein consisting of the sequence of SEQ ID NO:2, wherein said protein is produced in a non-human cell.

6. An isolated human MDM2 protein consisting of the sequence of SEQ ID NO:2.

7. An isolated human MDM2 protein consisting of the sequence of SEQ ID NO:2, wherein said protein is made in an in vitro transcription and translation system.

8. The human MDM2 protein of claim 6, wherein said human MDM2 protein is purified from other proteins using antibodies specifically immunoreactive with human MDM2 epitopes.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2372 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( H ) CELL LINE: CaCo-2

( v i i i ) POSITION IN GENOME:
        ( B ) MAP POSITION: 12q12-14

( i x ) FEATURE:
        ( A ) NAME/KEY: CDS
        ( B ) LOCATION: 312..1784

( x i ) SEQUENCE DESCRIPTION: SEQ ID NO:1:

```
GCACCGCGCG  AGCTTGGCTG  CTTCTGGGGC  CTGTGTGGCC  CTGTGTGTCG  GAAAGATGGA       60

GCAAGAAGCC  GAGCCCGAGG  GGCGGCCGCG  ACCCCTCTGA  CCGAGATCCT  GCTGCTTTCG      120

CAGCCAGGAG  CACCGTCCCT  CCCCGGATTA  GTGCGTACGA  GCGCCCAGTG  CCCTGGCCCG      180

GAGAGTGGAA  TGATCCCCGA  GGCCCAGGGC  GTCGTGCTTC  CGCAGTAGTC  AGTCCCCGTG      240

AAGGAAACTG  GGGAGTCTTG  AGGGACCCCC  GACTCCAAGC  GCGAAAACCC  CGGATGGTGA      300

GGAGCAGGCA A  ATG  TGC  AAT  ACC  AAC  ATG  TCT  GTA  CCT  ACT  GAT  GGT  GCT       350
             Met  Cys  Asn  Thr  Asn  Met  Ser  Val  Pro  Thr  Asp  Gly  Ala
              1                 5                               10

GTA  ACC  ACC  TCA  CAG  ATT  CCA  GCT  TCG  GAA  CAA  GAG  ACC  CTG  GTT  AGA       398
Val  Thr  Thr  Ser  Gln  Ile  Pro  Ala  Ser  Glu  Gln  Glu  Thr  Leu  Val  Arg
     15                      20                      25

CCA  AAG  CCA  TTG  CTT  TTG  AAG  TTA  TTA  AAG  TCT  GTT  GGT  GCA  CAA  AAA       446
Pro  Lys  Pro  Leu  Leu  Leu  Lys  Leu  Leu  Lys  Ser  Val  Gly  Ala  Gln  Lys
30                           35                      40                      45

GAC  ACT  TAT  ACT  ATG  AAA  GAG  GTT  CTT  TTT  TAT  CTT  GGC  CAG  TAT  ATT       494
Asp  Thr  Tyr  Thr  Met  Lys  Glu  Val  Leu  Phe  Tyr  Leu  Gly  Gln  Tyr  Ile
                     50                      55                      60

ATG  ACT  AAA  CGA  TTA  TAT  GAT  GAG  AAG  CAA  CAA  CAT  ATT  GTA  TAT  TGT       542
Met  Thr  Lys  Arg  Leu  Tyr  Asp  Glu  Lys  Gln  Gln  His  Ile  Val  Tyr  Cys
              65                      70                      75

TCA  AAT  GAT  CTT  CTA  GGA  GAT  TTG  TTT  GGC  GTG  CCA  AGC  TTC  TCT  GTG       590
Ser  Asn  Asp  Leu  Leu  Gly  Asp  Leu  Phe  Gly  Val  Pro  Ser  Phe  Ser  Val
         80                      85                      90

AAA  GAG  CAC  AGG  AAA  ATA  TAT  ACC  ATG  ATC  TAC  AGG  AAC  TTG  GTA  GTA       638
Lys  Glu  His  Arg  Lys  Ile  Tyr  Thr  Met  Ile  Tyr  Arg  Asn  Leu  Val  Val
     95                      100                     105

GTC  AAT  CAG  CAG  GAA  TCA  TCG  GAC  TCA  GGT  ACA  TCT  GTG  AGT  GAG  AAC       686
Val  Asn  Gln  Gln  Glu  Ser  Ser  Asp  Ser  Gly  Thr  Ser  Val  Ser  Glu  Asn
110                      115                     120                     125

AGG  TGT  CAC  CTT  GAA  GGT  GGG  AGT  GAT  CAA  AAG  GAC  CTT  GTA  CAA  GAG       734
Arg  Cys  His  Leu  Glu  Gly  Gly  Ser  Asp  Gln  Lys  Asp  Leu  Val  Gln  Glu
              130                     135                     140
```

```
CTT CAG GAA GAG AAA CCT TCA TCT TCA CAT TTG GTT TCT AGA CCA TCT        782
Leu Gln Glu Glu Lys Pro Ser Ser Ser His Leu Val Ser Arg Pro Ser
        145                 150                 155

ACC TCA TCT AGA AGG AGA GCA ATT AGT GAG ACA GAA GAA AAT TCA GAT        830
Thr Ser Ser Arg Arg Arg Ala Ile Ser Glu Thr Glu Glu Asn Ser Asp
        160                 165                 170

GAA TTA TCT GGT GAA CGA CAA AGA AAA CGC CAC AAA TCT GAT AGT ATT        878
Glu Leu Ser Gly Glu Arg Gln Arg Lys Arg His Lys Ser Asp Ser Ile
    175                 180                 185

TCC CTT TCC TTT GAT GAA AGC CTG GCT CTG TGT GTA ATA AGG GAG ATA        926
Ser Leu Ser Phe Asp Glu Ser Leu Ala Leu Cys Val Ile Arg Glu Ile
190                 195                 200                 205

TGT TGT GAA AGA AGC AGT AGC AGT GAA TCT ACA GGG ACG CCA TCG AAT        974
Cys Cys Glu Arg Ser Ser Ser Ser Glu Ser Thr Gly Thr Pro Ser Asn
                210                 215                 220

CCG GAT CTT GAT GCT GGT GTA AGT GAA CAT TCA GGT GAT TGG TTG GAT       1022
Pro Asp Leu Asp Ala Gly Val Ser Glu His Ser Gly Asp Trp Leu Asp
            225                 230                 235

CAG GAT TCA GTT TCA GAT CAG TTT AGT GTA GAA TTT GAA GTT GAA TCT       1070
Gln Asp Ser Val Ser Asp Gln Phe Ser Val Glu Phe Glu Val Glu Ser
            240                 245                 250

CTC GAC TCA GAA GAT TAT AGC CTT AGT GAA GAA GGA CAA GAA CTC TCA       1118
Leu Asp Ser Glu Asp Tyr Ser Leu Ser Glu Glu Gly Gln Glu Leu Ser
255                 260                 265

GAT GAA GAT GAT GAG GTA TAT CAA GTT ACT GTG TAT CAG GCA GGG GAG       1166
Asp Glu Asp Asp Glu Val Tyr Gln Val Thr Val Tyr Gln Ala Gly Glu
270                 275                 280                 285

AGT GAT ACA GAT TCA TTT GAA GAA GAT CCT GAA ATT TCC TTA GCT GAC       1214
Ser Asp Thr Asp Ser Phe Glu Glu Asp Pro Glu Ile Ser Leu Ala Asp
                290                 295                 300

TAT TGG AAA TGC ACT TCA TGC AAT GAA ATG AAT CCC CCC CTT CCA TCA       1262
Tyr Trp Lys Cys Thr Ser Cys Asn Glu Met Asn Pro Pro Leu Pro Ser
            305                 310                 315

CAT TGC AAC AGA TGT TGG GCC CTT CGT GAG AAT TGG CTT CCT GAA GAT       1310
His Cys Asn Arg Cys Trp Ala Leu Arg Glu Asn Trp Leu Pro Glu Asp
            320                 325                 330

AAA GGG AAA GAT AAA GGG GAA ATC TCT GAG AAA GCC AAA CTG GAA AAC       1358
Lys Gly Lys Asp Lys Gly Glu Ile Ser Glu Lys Ala Lys Leu Glu Asn
        335                 340                 345

TCA ACA CAA GCT GAA GAG GGC TTT GAT GTT CCT GAT TGT AAA AAA ACT       1406
Ser Thr Gln Ala Glu Glu Gly Phe Asp Val Pro Asp Cys Lys Lys Thr
350                 355                 360                 365

ATA GTG AAT GAT TCC AGA GAG TCA TGT GTT GAG GAA AAT GAT GAT AAA       1454
Ile Val Asn Asp Ser Arg Glu Ser Cys Val Glu Glu Asn Asp Asp Lys
                370                 375                 380

ATT ACA CAA GCT TCA CAA TCA CAA GAA AGT GAA GAC TAT TCT CAG CCA       1502
Ile Thr Gln Ala Ser Gln Ser Gln Glu Ser Glu Asp Tyr Ser Gln Pro
            385                 390                 395

TCA ACT TCT AGT AGC ATT ATT TAT AGC AGC CAA GAA GAT GTG AAA GAG       1550
Ser Thr Ser Ser Ser Ile Ile Tyr Ser Ser Gln Glu Asp Val Lys Glu
            400                 405                 410

TTT GAA AGG GAA GAA ACC CAA GAC AAA GAA GAG AGT GTG GAA TCT AGT       1598
Phe Glu Arg Glu Glu Thr Gln Asp Lys Glu Glu Ser Val Glu Ser Ser
    415                 420                 425

TTG CCC CTT AAT GCC ATT GAA CCT TGT GTG ATT TGT CAA GGT CGA CCT       1646
Leu Pro Leu Asn Ala Ile Glu Pro Cys Val Ile Cys Gln Gly Arg Pro
430                 435                 440                 445

AAA AAT GGT TGC ATT GTC CAT GGC AAA ACA GGA CAT CTT ATG GCC TGC       1694
Lys Asn Gly Cys Ile Val His Gly Lys Thr Gly His Leu Met Ala Cys
                450                 455                 460
```

```
TTT  ACA  TGT  GCA  AAG  AAG  CTA  AAG  AAA  AGG  AAT  AAG  CCC  TGC  CCA  GTA     1742
Phe  Thr  Cys  Ala  Lys  Lys  Leu  Lys  Lys  Arg  Asn  Lys  Pro  Cys  Pro  Val
               465                      470                      475

TGT  AGA  CAA  CCA  ATT  CAA  ATG  ATT  GTG  CTA  ACT  TAT  TTC  CCC               1784
Cys  Arg  Gln  Pro  Ile  Gln  Met  Ile  Val  Leu  Thr  Tyr  Phe  Pro
               480                      485                 490

TAGTTGACCT  GTCTATAAGA  GAATTATATA  TTTCTAACTA  TATAACCCTA  GGAATTTAGA             1844

CAACCTGAAA  TTTATTCACA  TATATCAAAG  TGAGAAAATG  CCTCAATTCA  CATAGATTTC             1904

TTCTCTTTAG  TATAATTGAC  CTACTTTGGT  AGTGGAATAG  TGAATACTTA  CTATAATTTG             1964

ACTTGAATAT  GTAGCTCATC  CTTTACACCA  ACTCCTAATT  TTAAATAATT  TCTACTCTGT             2024

CTTAAATGAG  AAGTACTTGG  TTTTTTTTTT  CTTAAATATG  TATATGACAT  TTAAATGTAA             2084

CTTATTATTT  TTTTGAGAC   CGAGTCTTGC  TCTGTTACCC  AGGCTGGAGT  GCAGTGGGTG             2144

ATCTTGGCTC  ACTGCAAGCT  CTGCCCTCCC  CGGGTTCGCA  CCATTCTCCT  GCCTCAGCCT             2204

CCCAATTAGC  TTGGCCTACA  GTCATCTGCC  ACCACACCTG  GCTAATTTTT  TGTACTTTTA             2264

GTAGAGACAG  GGTTTCACCG  TGTTAGCCAG  GATGGTCTCG  ATCTCCTGAC  CTCGTGATCC             2324

GCCCACCTCG  GCCTCCCAAA  GTGCTGGGAT  TACAGGCATG  AGCCACCG                           2372
```

( 2 ) INFORMATION FOR SEQ ID NO:2:

( i ) SEQUENCE CHARACTERISTICS:
        ( A ) LENGTH: 491 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Cys  Asn  Thr  Asn  Met  Ser  Val  Pro  Thr  Asp  Gly  Ala  Val  Thr  Thr
 1                   5                        10                       15

Ser  Gln  Ile  Pro  Ala  Ser  Glu  Gln  Glu  Thr  Leu  Val  Arg  Pro  Lys  Pro
                20                       25                       30

Leu  Leu  Leu  Lys  Leu  Leu  Lys  Ser  Val  Gly  Ala  Gln  Lys  Asp  Thr  Tyr
               35                       40                       45

Thr  Met  Lys  Glu  Val  Leu  Phe  Tyr  Leu  Gly  Gln  Tyr  Ile  Met  Thr  Lys
      50                        55                       60

Arg  Leu  Tyr  Asp  Glu  Lys  Gln  Gln  His  Ile  Val  Tyr  Cys  Ser  Asn  Asp
 65                       70                       75                       80

Leu  Leu  Gly  Asp  Leu  Phe  Gly  Val  Pro  Ser  Phe  Ser  Val  Lys  Glu  His
                    85                       90                       95

Arg  Lys  Ile  Tyr  Thr  Met  Ile  Tyr  Arg  Asn  Leu  Val  Val  Val  Asn  Gln
               100                      105                     110

Gln  Glu  Ser  Ser  Asp  Ser  Gly  Thr  Ser  Val  Ser  Glu  Asn  Arg  Cys  His
               115                      120                     125

Leu  Glu  Gly  Gly  Ser  Asp  Gln  Lys  Asp  Leu  Val  Gln  Glu  Leu  Gln  Glu
          130                      135                     140

Glu  Lys  Pro  Ser  Ser  Ser  His  Leu  Val  Ser  Arg  Pro  Ser  Thr  Ser  Ser
145                      150                     155                     160

Arg  Arg  Arg  Ala  Ile  Ser  Glu  Thr  Glu  Glu  Asn  Ser  Asp  Glu  Leu  Ser
                    165                      170                     175

Gly  Glu  Arg  Gln  Arg  Lys  Arg  His  Lys  Ser  Asp  Ser  Ile  Ser  Leu  Ser
               180                      185                     190

Phe  Asp  Glu  Ser  Leu  Ala  Leu  Cys  Val  Ile  Arg  Glu  Ile  Cys  Cys  Glu
          195                      200                     205
```

| Arg | Ser | Ser | Ser | Ser | Glu | Ser | Thr | Gly | Thr | Pro | Ser | Asn | Pro | Asp | Leu |
|---|---|---|---|---|---|---|---|---|---|---|---|---|---|---|---|
| 210 | | | | | 215 | | | | | 220 | | | | | |

| Asp | Ala | Gly | Val | Ser | Glu | His | Ser | Gly | Asp | Trp | Leu | Asp | Gln | Asp | Ser |
|---|---|---|---|---|---|---|---|---|---|---|---|---|---|---|---|
| 225 | | | | | 230 | | | | | 235 | | | | | 240 |

| Val | Ser | Asp | Gln | Phe | Ser | Val | Glu | Phe | Glu | Val | Glu | Ser | Leu | Asp | Ser |
|---|---|---|---|---|---|---|---|---|---|---|---|---|---|---|---|
| | | | | 245 | | | | | 250 | | | | | 255 | |

| Glu | Asp | Tyr | Ser | Leu | Ser | Glu | Glu | Gly | Gln | Glu | Leu | Ser | Asp | Glu | Asp |
|---|---|---|---|---|---|---|---|---|---|---|---|---|---|---|---|
| | | | 260 | | | | | 265 | | | | | 270 | | |

| Asp | Glu | Val | Tyr | Gln | Val | Thr | Val | Tyr | Gln | Ala | Gly | Glu | Ser | Asp | Thr |
|---|---|---|---|---|---|---|---|---|---|---|---|---|---|---|---|
| | | 275 | | | | | 280 | | | | | 285 | | | |

| Asp | Ser | Phe | Glu | Glu | Asp | Pro | Glu | Ile | Ser | Leu | Ala | Asp | Tyr | Trp | Lys |
|---|---|---|---|---|---|---|---|---|---|---|---|---|---|---|---|
| | 290 | | | | | 295 | | | | | 300 | | | | |

| Cys | Thr | Ser | Cys | Asn | Glu | Met | Asn | Pro | Pro | Leu | Pro | Ser | His | Cys | Asn |
|---|---|---|---|---|---|---|---|---|---|---|---|---|---|---|---|
| 305 | | | | | 310 | | | | | 315 | | | | | 320 |

| Arg | Cys | Trp | Ala | Leu | Arg | Glu | Asn | Trp | Leu | Pro | Glu | Asp | Lys | Gly | Lys |
|---|---|---|---|---|---|---|---|---|---|---|---|---|---|---|---|
| | | | | 325 | | | | | 330 | | | | | 335 | |

| Asp | Lys | Gly | Glu | Ile | Ser | Glu | Lys | Ala | Lys | Leu | Glu | Asn | Ser | Thr | Gln |
|---|---|---|---|---|---|---|---|---|---|---|---|---|---|---|---|
| | | | 340 | | | | | 345 | | | | | 350 | | |

| Ala | Glu | Glu | Gly | Phe | Asp | Val | Pro | Asp | Cys | Lys | Lys | Thr | Ile | Val | Asn |
|---|---|---|---|---|---|---|---|---|---|---|---|---|---|---|---|
| | | 355 | | | | | 360 | | | | | 365 | | | |

| Asp | Ser | Arg | Glu | Ser | Cys | Val | Glu | Glu | Asn | Asp | Asp | Lys | Ile | Thr | Gln |
|---|---|---|---|---|---|---|---|---|---|---|---|---|---|---|---|
| | 370 | | | | | 375 | | | | | 380 | | | | |

| Ala | Ser | Gln | Ser | Gln | Glu | Ser | Glu | Asp | Tyr | Ser | Gln | Pro | Ser | Thr | Ser |
|---|---|---|---|---|---|---|---|---|---|---|---|---|---|---|---|
| 385 | | | | | 390 | | | | | 395 | | | | | 400 |

| Ser | Ser | Ile | Ile | Tyr | Ser | Ser | Gln | Glu | Asp | Val | Lys | Glu | Phe | Glu | Arg |
|---|---|---|---|---|---|---|---|---|---|---|---|---|---|---|---|
| | | | | 405 | | | | | 410 | | | | | 415 | |

| Glu | Glu | Thr | Gln | Asp | Lys | Glu | Glu | Ser | Val | Glu | Ser | Ser | Leu | Pro | Leu |
|---|---|---|---|---|---|---|---|---|---|---|---|---|---|---|---|
| | | | 420 | | | | | 425 | | | | | 430 | | |

| Asn | Ala | Ile | Glu | Pro | Cys | Val | Ile | Cys | Gln | Gly | Arg | Pro | Lys | Asn | Gly |
|---|---|---|---|---|---|---|---|---|---|---|---|---|---|---|---|
| | | 435 | | | | | 440 | | | | | 445 | | | |

| Cys | Ile | Val | His | Gly | Lys | Thr | Gly | His | Leu | Met | Ala | Cys | Phe | Thr | Cys |
|---|---|---|---|---|---|---|---|---|---|---|---|---|---|---|---|
| | 450 | | | | | 455 | | | | | 460 | | | | |

| Ala | Lys | Lys | Leu | Lys | Lys | Arg | Asn | Lys | Pro | Cys | Pro | Val | Cys | Arg | Gln |
|---|---|---|---|---|---|---|---|---|---|---|---|---|---|---|---|
| 465 | | | | | 470 | | | | | 475 | | | | | 480 |

| Pro | Ile | Gln | Met | Ile | Val | Leu | Thr | Tyr | Phe | Pro |
|---|---|---|---|---|---|---|---|---|---|---|
| | | | | 485 | | | | | 490 | |

( 2 ) INFORMATION FOR SEQ ID NO:3:

( i ) SEQUENCE CHARACTERISTICS:
        ( A ) LENGTH: 1710 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mus musculus ( i x ) FEATURE:
        ( A ) NAME/KEY: CDS
        ( B ) LOCATION: 202..1668

( x i ) SEQUENCE DESCRIPTION: SEQ ID NO:3:

GAGGAGCCGC CGCCTTCTCG TCGCTCGAGC TCTGGACGAC CATGGTCGCT CAGGCCCCGT     60

-continued

| | | | | | |
|---|---|---|---|---|---|
| CCGCGGGGCC | TCCGCGCTCC | CCGTGAAGGG | TCGGAAGATG | CGCGGGAAGT | AGCAGCCGTC | 120 |
| TGCTGGGCGA | GCGGGAGACC | GACCGGACAC | CCCTGGGGGA | CCCTCTCGGA | TCACCGCGCT | 180 |

```
TCTCCTGCGG CCTCCAGGCC A ATG TGC AAT ACC AAC ATG TCT GTG TCT ACC           231
                         Met Cys Asn Thr Asn Met Ser Val Ser Thr
                          1               5                  10

GAG GGT GCT GCA AGC ACC TCA CAG ATT CCA GCT TCG GAA CAA GAG ACT           279
Glu Gly Ala Ala Ser Thr Ser Gln Ile Pro Ala Ser Glu Gln Glu Thr
                15                  20                  25

CTG GTT AGA CCA AAA CCA TTG CTT TTG AAG TTG TTA AAG TCC GTT GGA           327
Leu Val Arg Pro Lys Pro Leu Leu Leu Lys Leu Leu Lys Ser Val Gly
            30                  35                  40

GCG CAA AAC GAC ACT TAC ACT ATG AAA GAG ATT ATA TTT TAT ATT GGC           375
Ala Gln Asn Asp Thr Tyr Thr Met Lys Glu Ile Ile Phe Tyr Ile Gly
        45                  50                  55

CAG TAT ATT ATG ACT AAG AGG TTA TAT GAC GAG AAG CAG CAG CAC ATT           423
Gln Tyr Ile Met Thr Lys Arg Leu Tyr Asp Glu Lys Gln Gln His Ile
    60                  65                  70

GTG TAT TGT TCA AAT GAT CTC CTA GGA GAT GTG TTT GGA GTC CCG AGT           471
Val Tyr Cys Ser Asn Asp Leu Leu Gly Asp Val Phe Gly Val Pro Ser
75                  80                  85                  90

TTC TCT GTG AAG GAG CAC AGG AAA ATA TAT GCA ATG ATC TAC AGA AAT           519
Phe Ser Val Lys Glu His Arg Lys Ile Tyr Ala Met Ile Tyr Arg Asn
                95                  100                 105

TTA GTG GCT GTA AGT CAG CAA GAC TCT GGC ACA TCG CTG AGT GAG AGC           567
Leu Val Ala Val Ser Gln Gln Asp Ser Gly Thr Ser Leu Ser Glu Ser
            110                 115                 120

AGA CGT CAG CCT GAA GGT GGG AGT GAT CTG AAG GAT CCT TTG CAA GCG           615
Arg Arg Gln Pro Glu Gly Gly Ser Asp Leu Lys Asp Pro Leu Gln Ala
        125                 130                 135

CCA CCA GAA GAG AAA CCT TCA TCT TCT GAT TTA ATT TCT AGA CTG TCT           663
Pro Pro Glu Glu Lys Pro Ser Ser Ser Asp Leu Ile Ser Arg Leu Ser
    140                 145                 150

ACC TCA TCT AGA AGG AGA TCC ATT AGT GAG ACA GAA GAG AAC ACA GAT           711
Thr Ser Ser Arg Arg Arg Ser Ile Ser Glu Thr Glu Glu Asn Thr Asp
155                 160                 165                 170

GAG CTA CCT GGG GAG CGG CAC CGG AAG CGC CGC AGG TCC CTG TCC TTT           759
Glu Leu Pro Gly Glu Arg His Arg Lys Arg Arg Arg Ser Leu Ser Phe
                175                 180                 185

GAT CCG AGC CTG GGT CTG TGT GAG CTG AGG GAG ATG TGC AGC GGC GGC           807
Asp Pro Ser Leu Gly Leu Cys Glu Leu Arg Glu Met Cys Ser Gly Gly
            190                 195                 200

ACG AGC AGC AGT AGC AGC AGC AGC GAG TCC ACA GAG ACG CCC TCG           855
Thr Ser Ser Ser Ser Ser Ser Ser Glu Ser Thr Glu Thr Pro Ser
        205                 210                 215

CAT CAG GAT CTT GAC GAT GGC GTA AGT GAG CAT TCT GGT GAT TGC CTG           903
His Gln Asp Leu Asp Asp Gly Val Ser Glu His Ser Gly Asp Cys Leu
    220                 225                 230

GAT CAG GAT TCA GTT TCT GAT CAG TTT AGC GTG GAA TTT GAA GTT GAG           951
Asp Gln Asp Ser Val Ser Asp Gln Phe Ser Val Glu Phe Glu Val Glu
235                 240                 245                 250

TCT CTG GAC TCG GAA GAT TAC AGC CTG AGT GAC GAA GGG CAC GAG CTC           999
Ser Leu Asp Ser Glu Asp Tyr Ser Leu Ser Asp Glu Gly His Glu Leu
                255                 260                 265

TCA GAT GAG GAT GAT GAG GTC TAT CGG GTC ACA GTC TAT CAG ACA GGA          1047
Ser Asp Glu Asp Asp Glu Val Tyr Arg Val Thr Val Tyr Gln Thr Gly
            270                 275                 280

GAA AGC GAT ACA GAC TCT TTT GAA GGA GAT CCT GAG ATT TCC TTA GCT          1095
Glu Ser Asp Thr Asp Ser Phe Glu Gly Asp Pro Glu Ile Ser Leu Ala
        285                 290                 295
```

```
GAC  TAT  TGG  AAG  TGT  ACC  TCA  TGC  AAT  GAA  ATG  AAT  CCT  CCC  CTT  CCA      1143
Asp  Tyr  Trp  Lys  Cys  Thr  Ser  Cys  Asn  Glu  Met  Asn  Pro  Pro  Leu  Pro
          300                 305                 310

TCA  CAC  TGC  AAA  AGA  TGC  TGG  ACC  CTT  CGT  GAG  AAC  TGG  CTT  CCA  GAC      1191
Ser  His  Cys  Lys  Arg  Cys  Trp  Thr  Leu  Arg  Glu  Asn  Trp  Leu  Pro  Asp
315                      320                 325                           330

GAT  AAG  GGG  AAA  GAT  AAA  GTG  GAA  ATC  TCT  GAA  AAA  GCC  AAA  CTG  GAA      1239
Asp  Lys  Gly  Lys  Asp  Lys  Val  Glu  Ile  Ser  Glu  Lys  Ala  Lys  Leu  Glu
                    335                 340                      345

AAC  TCA  GCT  CAG  GCA  GAA  GAA  GGC  TTG  GAT  GTG  CCT  GAT  GGC  AAA  AAG      1287
Asn  Ser  Ala  Gln  Ala  Glu  Glu  Gly  Leu  Asp  Val  Pro  Asp  Gly  Lys  Lys
               350                      355                      360

CTG  ACA  GAG  AAT  GAT  GCT  AAA  GAG  CCA  TGT  GCT  GAG  GAG  GAC  AGC  GAG      1335
Leu  Thr  Glu  Asn  Asp  Ala  Lys  Glu  Pro  Cys  Ala  Glu  Glu  Asp  Ser  Glu
          365                      370                      375

GAG  AAG  GCC  GAA  CAG  ACG  CCC  CTG  TCC  CAG  GAG  AGT  GAC  GAC  TAT  TCC      1383
Glu  Lys  Ala  Glu  Gln  Thr  Pro  Leu  Ser  Gln  Glu  Ser  Asp  Asp  Tyr  Ser
     380                      385                      390

CAA  CCA  TCG  ACT  TCC  AGC  AGC  ATT  GTT  TAT  AGC  AGC  CAA  GAA  AGC  GTG      1431
Gln  Pro  Ser  Thr  Ser  Ser  Ser  Ile  Val  Tyr  Ser  Ser  Gln  Glu  Ser  Val
395                           400                 405                      410

AAA  GAG  TTG  AAG  GAG  GAA  ACG  CAG  CAC  AAA  GAC  GAG  AGT  GTG  GAA  TCT      1479
Lys  Glu  Leu  Lys  Glu  Glu  Thr  Gln  His  Lys  Asp  Glu  Ser  Val  Glu  Ser
                    415                      420                      425

AGC  TTC  TCC  CTG  AAT  GCC  ATC  GAA  CCA  TGT  GTG  ATC  TGC  CAG  GGG  CGG      1527
Ser  Phe  Ser  Leu  Asn  Ala  Ile  Glu  Pro  Cys  Val  Ile  Cys  Gln  Gly  Arg
               430                      435                      440

CCT  AAA  AAT  GGC  TGC  ATT  GTT  CAC  GGC  AAG  ACT  GGA  CAC  CTC  ATG  TCA      1575
Pro  Lys  Asn  Gly  Cys  Ile  Val  His  Gly  Lys  Thr  Gly  His  Leu  Met  Ser
          445                      450                      455

TGT  TTC  ACG  TGT  GCA  AAG  AAG  CTA  AAA  AAA  AGA  AAC  AAG  CCC  TGC  CCA      1623
Cys  Phe  Thr  Cys  Ala  Lys  Lys  Leu  Lys  Lys  Arg  Asn  Lys  Pro  Cys  Pro
     460                      465                      470

GTG  TGC  AGA  CAG  CCA  ATC  CAA  ATG  ATT  GTG  CTA  AGT  TAC  TTC  AAC           1668
Val  Cys  Arg  Gln  Pro  Ile  Gln  Met  Ile  Val  Leu  Ser  Tyr  Phe  Asn
475                      480                      485

TAGCTGACCT  GCTCACAAAA  ATAGAATTTT  ATATTTCTAA  CT                                  1710
```

( 2 ) INFORMATION FOR SEQ ID NO:4:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Cys  Asn  Thr  Asn  Met  Ser  Val  Ser  Thr  Glu  Gly  Ala  Ala  Ser  Thr
 1                   5                   10                       15

Ser  Gln  Ile  Pro  Ala  Ser  Glu  Gln  Glu  Thr  Leu  Val  Arg  Pro  Lys  Pro
               20                   25                       30

Leu  Leu  Leu  Lys  Leu  Leu  Lys  Ser  Val  Gly  Ala  Gln  Asn  Asp  Thr  Tyr
          35                   40                       45

Thr  Met  Lys  Glu  Ile  Ile  Phe  Tyr  Ile  Gly  Gln  Tyr  Ile  Met  Thr  Lys
     50                   55                       60

Arg  Leu  Tyr  Asp  Glu  Lys  Gln  Gln  His  Ile  Val  Tyr  Cys  Ser  Asn  Asp
65                   70                       75                            80

Leu  Leu  Gly  Asp  Val  Phe  Gly  Val  Pro  Ser  Phe  Ser  Val  Lys  Glu  His
                85                        90                       95
```

| | | | | | | | | | | | | | | |
|---|---|---|---|---|---|---|---|---|---|---|---|---|---|---|
| Arg | Lys | Ile | Tyr 100 | Ala | Met | Ile | Tyr 105 | Arg | Asn | Leu | Val | Ala 110 | Val | Ser | Gln |
| Gln | Asp | Ser 115 | Gly | Thr | Ser | Leu | Ser 120 | Glu | Ser | Arg | Arg 125 | Gln | Pro | Glu | Gly |
| Gly 130 | Ser | Asp | Leu | Lys | Asp 135 | Pro | Leu | Gln | Ala | Pro 140 | Pro | Glu | Glu | Lys | Pro |
| Ser 145 | Ser | Ser | Asp | Leu | Ile 150 | Ser | Arg | Leu | Ser | Thr 155 | Ser | Ser | Arg | Arg | Arg 160 |
| Ser | Ile | Ser | Glu | Thr 165 | Glu | Glu | Asn | Thr | Asp 170 | Glu | Leu | Pro | Gly | Glu 175 | Arg |
| His | Arg | Lys | Arg 180 | Arg | Arg | Ser | Leu | Ser 185 | Phe | Asp | Pro | Ser | Leu 190 | Gly | Leu |
| Cys | Glu | Leu 195 | Arg | Glu | Met | Cys | Ser 200 | Gly | Gly | Thr | Ser | Ser 205 | Ser | Ser | Ser |
| Ser | Ser 210 | Ser | Glu | Ser | Thr | Glu 215 | Thr | Pro | Ser | His | Gln 220 | Asp | Leu | Asp | Asp |
| Gly 225 | Val | Ser | Glu | His | Ser 230 | Gly | Asp | Cys | Leu | Asp 235 | Gln | Asp | Ser | Val | Ser 240 |
| Asp | Gln | Phe | Ser | Val 245 | Glu | Phe | Glu | Val | Glu 250 | Ser | Leu | Asp | Ser | Glu 255 | Asp |
| Tyr | Ser | Leu | Ser 260 | Asp | Glu | Gly | His | Glu 265 | Leu | Ser | Asp | Glu | Asp 270 | Asp | Glu |
| Val | Tyr | Arg 275 | Val | Thr | Val | Tyr | Gln 280 | Thr | Gly | Glu | Ser | Asp 285 | Thr | Asp | Ser |
| Phe | Glu 290 | Gly | Asp | Pro | Glu | Ile 295 | Ser | Leu | Ala | Asp | Tyr 300 | Trp | Lys | Cys | Thr |
| Ser 305 | Cys | Asn | Glu | Met | Asn 310 | Pro | Pro | Leu | Pro | Ser 315 | His | Cys | Lys | Arg | Cys 320 |
| Trp | Thr | Leu | Arg | Glu 325 | Asn | Trp | Leu | Pro | Asp 330 | Asp | Lys | Gly | Lys | Asp 335 | Lys |
| Val | Glu | Ile | Ser 340 | Glu | Lys | Ala | Lys | Leu 345 | Glu | Asn | Ser | Ala | Gln 350 | Ala | Glu |
| Glu | Gly | Leu 355 | Asp | Val | Pro | Asp | Gly 360 | Lys | Lys | Leu | Thr | Glu 365 | Asn | Asp | Ala |
| Lys | Glu 370 | Pro | Cys | Ala | Glu | Glu 375 | Asp | Ser | Glu | Glu | Lys 380 | Ala | Glu | Gln | Thr |
| Pro 385 | Leu | Ser | Gln | Glu | Ser 390 | Asp | Asp | Tyr | Ser | Gln 395 | Pro | Ser | Thr | Ser | Ser 400 |
| Ser | Ile | Val | Tyr | Ser 405 | Ser | Gln | Glu | Ser | Val 410 | Lys | Glu | Leu | Lys | Glu 415 | Glu |
| Thr | Gln | His | Lys 420 | Asp | Glu | Ser | Val | Glu 425 | Ser | Ser | Phe | Ser | Leu 430 | Asn | Ala |
| Ile | Glu | Pro 435 | Cys | Val | Ile | Cys | Gln 440 | Gly | Arg | Pro | Lys | Asn 445 | Gly | Cys | Ile |
| Val | His 450 | Gly | Lys | Thr | Gly | His 455 | Leu | Met | Ser | Cys | Phe 460 | Thr | Cys | Ala | Lys |
| Lys 465 | Leu | Lys | Lys | Arg | Asn 470 | Lys | Pro | Cys | Pro | Val 475 | Cys | Arg | Gln | Pro | Ile 480 |
| Gln | Met | Ile | Val | Leu 485 | Ser | Tyr | Phe | Asn | | | | | | | |